United States Patent [19]

Barton

[11] Patent Number: 4,999,300
[45] Date of Patent: Mar. 12, 1991

[54] BACTERIAL DEGRADATION OF 4-CHLOROBIPHENYL

[75] Inventor: Marlene R. Barton, St. Louis Park, Minn.

[73] Assignee: Regents of the University of Minnesota, Minneapolis, Minn.

[21] Appl. No.: 173,992

[22] Filed: Mar. 28, 1988

[51] Int. Cl.$^5$ .................. C12N 1/22; C12N 1/20; C02F 3/00

[52] U.S. Cl. .................. 435/252.34; 435/253.3; 435/262; 210/610

[58] Field of Search ............. 435/252.34, 253.3, 262; 210/601

[56] References Cited

PUBLICATIONS

Furukawa, *Biodegradation and Detoxification of Environmental Pollutants*, (CRC Press 1982), pp. 34–57.
Jacobson et al., *Developmental Psychology*, 20: 523–532 (1984).
Fishbein, *Annual Review of Pharmacology*, 14: 139–156 (1984).
Rehfeld, et al., *Poultry Science*, 50: 1090–1096 (1971).
Vos et al., *Toxicology and Applied Pharmacology*, 17: 656–668 (1970).
Furakawa, *Applied Environmental Microbiology*, 35: 223–227 (1978).
Wallnoffer and Englehardt, *Chemosphere*, 2: 69–72 (1973).
Ahmed and Focht, *Canadian Journal of Microbiology*, 19: 47–52 (1973).
Masse et al., *Applied and Environmental Microbiology*, 47: 947–951 (1984).
Sylvestre and Fauteux, *Journal of General Application of Microbiology*, 28: 61–72 (1982).
Sylvestre et al., *Applied Microbiology and Biotechnology*, 21: 192–195 (1985).
Maniatis et al., *Molecular Cloning*, p. 368–369 (Spring Harbor Lab. Pub. 1982).
Gibson, *Science*, 161: 1093–1097 (1968).
Furukawa dn Matsumura, *Journal of Agriculture Food Chemistry*, 24: 251–256 (1976).
Bedard, et al., *Applied and Environmental Microbiology*, 51: 761–768 (1986).
Dagley, *Essays in Biochemistry*, 11: 81–138 (1975).
Catelini and Colombi, *Biochemistry Journal*, 143: 431–434 (1974).
Chakrabarty et al., *Proc. Natl. Acad. Sci. U.S.A.;* 75: 3109–3112 (1978).
Clark et al., *Applied and Environmental Microbiology*, 37: 680–685 (1979).
Dagley, *Developments in Industrial Microbiology*, 25: 53–65 (1984).
Dagley, *Catabolism of Aromatic Compounds by Micro-Organisms*, pp. 1–46.
Dagley et al., *Nature*, 188: 560–566 (1960).
Eckhardt, *Plasmid*, 1: 584–588 (1978).
Furukawa and Chakrabarty, *Applied and Environmental Microbiology*, 44: 619–626 (1982).
Furukawa et al., *Applied and Environmental Microbiology*, 38: 301–310 (1979).
Furukawa et al.; *Applied and Environmental Microbiology*, 46: 140–145 (1983).
Gibson et al., *Biochemistry*, 7: 3795–3802 (1968).
Greenwood, *Microbiology Series*, 16: 1–17 (1985).
Horvath, *Bacteriological Review*, 36: 146–155 (1972).
Safe, *Microbial Degradation of Polychlorinated Biphenyls*, pp. 361–369.
Skinner and Lovelock, *The Society for Applied Bacteriology* Technical Series No. 14; pp. 1–14 (1979).
Sylvestre, *Applied and Environmental Microbiology*, 39: 1223–1224 (1980).
Sylvestre et al.; *Applied and Environmental Microbiology*, 44: 871–877 (1982).
Thomas et al., *Applied and Environmental Microbiology*, 52: 290–296 (1986).
Wyndham et al.; *Research Communications in Chemical Pathology and Pharmacology*, 15: 563–570 (1976).
Bergey's; Determinative Bacteriology; pp. 618–620, pp. 217–221, pp. 436–437, pp. 273–274 (Williams & Wilkins, 1974).

Primary Examiner—Robin L. Teskin
Assistant Examiner—Joan Ellis
Attorney, Agent, or Firm—Merchant, Gould, Smith, Edell, Welter & Schmidt

[57] ABSTRACT

A novel strain of *Pseudomonas* capable of utilizing 4-chlorobiphenyl as sole carbon and energy source is disclosed. The bacterium identified as *Pseudomonas* MB86 is shown to degrade 4-chlorobiphenyl to 4'-chloroacetophenone and other metabolites.

1 Claim, 14 Drawing Sheets

BACTERIAL DEGRADATION OF 4-CHLOROBIPHENYL

TECHNICAL FIELD

This invention relates to degradation of 4-chlorobiphenyl by a strain of Pseudomonas bacteria. The novel strain of bacteria, Pseudomonas MB86, is capable of utilizing 4-chlorobiphenyl.

BACKGROUND

Polychlorinated biphenyls (PCBs) represent a class of toxic xenobiotic chemicals that are distributed throughout the biosphere. Over the past several years, PCBs have received ever-increasing attention due to concerns about their toxicity and potential carcinogenicity. PCBs are produced by direct chlorination of biphenyl. Due to the large number of hydrogen atoms present on the biphenyl nucleus, many different chlorinated species (termed "congeners⇌) are possible. As many as 210 congeners of the PCBs could be theoretically produced [Furukawa, *Biodegradation and Detoxification of Environmental Pollutants*, p. 44–57 (CRC Press 1982)]; however, due to steric restrictions, only about half this number are actually observed. Therefore, PCBs are mixtures of a variety of chlorine-substituted biphenyl molecules.

PCBs have been widely used industrially due largely to their thermal stability and flame retardance. Such characteristics encouraged PCB use in transformer oils and in other high-temperature applications. Until the early 1970's PCBs were found in various pesticide formulations. PCBs have also been used in plasticizers, heat transfer and capacitor systems, surface coatings, printing inks, carbonless duplication paper, and waxes. While industrial use of PCB has been sharply restricted significant quantities of PCBs are still being released into the environment from waste dumps and failures of old electrical equipment. PCB contamination has been observed in drinking water, wastewater, foods, and especially in fish.

PCBs are lipophilic. They accumulate and are bioenhanced in fatty tissues [Furukawa supra; Jacobson et al., *Develop. Psychol.*, 20:523–532, (1984)]The physical effects of polychlorinated biphenyls vary from mammals, to birds, to humans. Mammals exposed to these chemicals exhibit marked changes in the liver [Fishbein, *Ann. Rev. Pharmocol.*, 14:139–156, (1974)], including lesions, fatty infiltration, centrolobular atrophy necrosis, and liver cell enlargement. In the case of rats, hyaline degeneration, are evidence of such exposure. Among the adverse physical effects exhibited in birds, kidney damage, fluid around the heart, intestinal hemorrhage, and reduced spleen size, have been observed [See Rehfeld et al., *Poultry Sci.* 50:1090–1096, (1971)]. Dermatitis from surface exposure can occur in both mammals and birds [Voss et al., *Toxicol. Appl. Pharmacol.*, 17:656–658 (1971)]. In addition to toxicity, PCBs may be carcinogenic and mutagenic (Fishbein, supra).

PCBs are not easily removed by natural microbial populations. In 1978, Furukawa et al., *Applied Environ. Micro.*, 35:223–227 studied the biodegradability of several isomers of polychlorinated biphenyls. They found that as chlorine substitution increased, degradability decreased. An isomer with four or more chlorines was not easily degraded. The position of the chlorine was also important. Ortho positioning of two chlorines on a single ring greatly inhibited degradation. If all the chlorines were on the same ring, degradation occurred at a faster rate than for isomers with the same number of chlorines spread over both rings. It was noted that ring fission usually took place on the lesser or non-chlorinated ring. These results suggested that PCBs could be utilized by bacteria, but only in certain isomeric forms. The products of such degradation were usually chlorinated. Subsequent studies have verified these observations.

Considering the environmental importance of PCBs and the hazards they pose, numerous investigators have been examining biological detoxification systems to deal with PCBs. One way to decipher the complexities of highly chlorinated isomers is to look at lesser chlorinated isomers. One of these which has been studied is 4-chlorobiphenyl.

4-chlorobiphenyl is one of the three monochlorinated isomers that can result from the chlorination of biphenyl. As with the other biphenyls, it is very insoluble in water, but freely soluble in a variety of organic solvents. Pure 4-chlorobiphenyl is crystalline, white to off-white in color. It is classified as an irritant.

Unlike the highly chlorinated biphenyls, a number of microorganisms have been identified that can degrade 4-chlorobiphenyl. Wallnofer and Englehardt *Chemosphere*, 2:69–73 (1973) isolated a soil fungus, *Rhizopus japonicus*, which hydroxylated 4-chlorobiphenyl at the 4' position. Other intermediates were not noted. In 1973, Ahmed and Focht, *Can. J. Microbiol*, 19:47–52 discovered a species of *Achromobacter* which produced 4-chlorobenzoic acid from 4-chlorobiphenyl. A study by Masse et al. *Appl. Environ. Micro.*, 47:947–951 (1984) also described the presence of 4-chlorobenzoate as a major metabolite of 4-chlorobiphenyl.

In 1982, Sylvestre and Fauteux *J. Gen. Appl. Micro.*, 28:61–72, reported a facultative anaerobe able to utilize 4-chlorobiphenyl. Up until that time, only strict aerobes were reported to degrade the lesser chlorinated PCB isomers. This organism was tentatively identified as a member of the bacterial group IVe. As with other 4-chlorohiphenyl degraders, 4-chlorobenzoic acid accumulated in the culture media.

Sylvestre et al. *Appl. Microbiol. Biotechnol.*, 21:192–195 (1985) reported that a two-membered bacterial culture was able to degrade both 4-chlorobiphenyl and 4-chlorobenzoate rapidly. An axenic culture was able to degrade 4-chlorobiphenyl alone, with a 45% decrease in substrate remaining after eight days. When incubated with a 4-chlorobenzoate degrader, 99% of the 4-chlorobiphenyl was degraded over the same time frame. However, no organism, to date, has been isolated which is able to grow on 4-chlorobiphenyl and degrade 4-chlorobiphenyl to 4'-chloroacetophenone and other metabolites.

SUMMARY OF INVENTION

We have discovered a bacteria of the genus Pseudomonas which is capable of degrading 4-chlorobiphenyl. The bacteria identified as *Pseudomonas MB86* can utilize 4-chlorobiphenyl.

The present invention comprises a biologically pure strain of the genus Pseudomonas having the characteristics of ATCC Deposit No. 53728 and the mutations thereof. The present invention can be used to degrade 4-chlorobiphenyl by cultivating a media containing 4-chlorobiphenyl with an effective amount of Pseudomonas MB86 cells. Pseudomonas MB86 is capable of sustaining growth in medium concentrations of 4-chlorobiphenyl from about 10 mg/50 ml to about 100 mg/50 ml. Preferably the organism is capable of sustaining growth in medium concentrations of 4-chlorobiphenyl up to 50 mg/50 ml.

BRIEF DESCRIPTION OF THE DRAWINGS

FIGS. 714 8 show gas-chromatograph/mass spectra of 2-hydroxy, 2-[4'-chlorophenyl] ethane standard and metabolite extracted from Pseudomonas MB86 culture fluid, respectively.

FIG. 14 shows electrophoresis of alkaline "miniprep" lysates of Pseudomonas MB86.

DETAILED DESCRIPTION OF THE INVENTION

Figure 1:
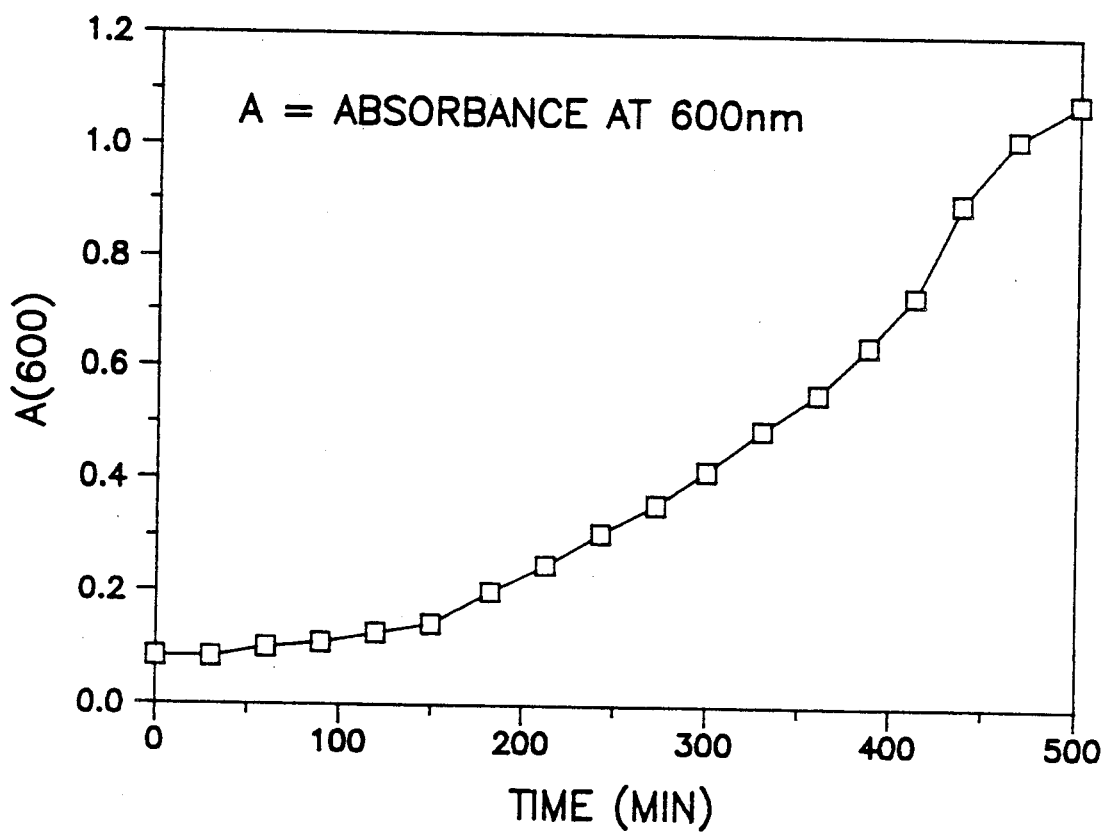
FIG. 1 shows a growth curve of Pseudomonas MB86 in 0.25% yeast extract broth.

A novel strain of Pseudomonas desiqnated as Pseudomonas MB8 6 capable of degrading 4-chlorobiphenyl and producing 4'-chloroacetophenone as a major metabolite was obtained and characterized using the materials and methods described below.

CULTURE MEDIA

A defined mineral salts medium was prepared from stock solutions of ten times concentrated buffer and ten times concentrated trace metals solutions. The stock buffer solution contained 42.50 g $K_2HPO_4.3H_2O$, 10.00 g $NaH_2PO_4.H_2O$ and 20.00 g $NH_4Cl$ per liter of distilled water. The stock trace metals solution contained 1.00 g nitrilotriacetic acid, 2.00 g $MgSO_4.7H_2O$, 0.12 g $FeSO_4.7H_2O$, 0.03 g $MnSO_4.H_2O$, 0.03 g $ZnSO_4.H_2O$, and 0.01 g $CaCl_2.5H_2O$ per liter of distilled water. One liter of growth medium consisted of 800 ml of distilled, deionized water and 100 ml of each of the 10X stock solution. The pH was adjusted to 7.45 with 6N NaOH. The resulting solution constituted basal medium.

After autoclaving, 4-chlorobiphenyl (1 mg/ml) was added directly and the medium was inoculated with Pseudomonas MB86 (a loopful of culture when taken from plates; 1 ml to 50 mls from liquid cultures—depending on culture size 50 ml up to 1000 ml). In addition to use as a broth, Noble agar (Difco) was added at 15.00 g per liter to the defined medium for substrate-free plates. 4-chlorobiphenyl crystals (approximately 10 mg) were placed in the lid of petri plates. Vaporization of the crystals provided a source of carbon and energy for Pseudomonas MB86 streaked onto the agar surface. Other carbon sources (yeast extract, 4-chlorobenzoate, etc.) were added directly to the medium as required (yeast extracts 0.25%; 4-chlorobenzoate 0.025%, 0.050%; 3-chlorobenzoate 0.025%, 0.050%). Subsequently, these plates were utilized for screening the organism's ability to utilize specific substrates as sources of carbon for growth and to maintain Pseudomonas MB86.

The same basal medium was used to prepare liquid or plated media containing alternate carbon sources such as yeast extract, 3-chlorobenzoate, 4-chlorobenzoate, 3-5,dichlorobenzoate, 4-hydroxybenzoate and sodium benzoate. Those volatile aromatic compounds that were insoluble in water, such as liquid 2-chlorobiphenyl (2-3 drops), liquid 3-chlorobiphenyl (2-3 drops), solid, crystalline biphenyl (10 mg up to 30 mg), and liquid 4'-chloroacetophenone (2-3 drops) were provided as carbon sources by placing the above indicated amounts into cotton-filled Durham tubes taped to the inside of the plate lid (for liquid compounds). Solid, volatile substrates (5-10 mg) were placed in the lid, as for 4-chlorobiphenyl. Most incubations were performed at 30° C, with liquids placed on a rotary shaker at 200 rpm.

MEDIA USED FOR GENUS IDENTIFICATION

Preliminary screenings of cultural characteristics of the bacterium were accomplished utilizing Klinger Triple Sugar Iron agar, SIMS media, Eosin Methylene Blue plates. Final identification was performed utilizing an OxiFerm tube from Roche Labs. (A control was run using a known culture of Pseudomonas aeruginosa to ensure that the Oxiferm tubes were running correctly.) Other tests were done utilizing Pseudomonas A and B agar, DNase plates, blood agar, and glucose, sucrose, and lactose broths obtained from the University of Minnesota microbiology preparatory labs. To determine oxygen requirements, yeast extract plates (0.25% yeast extract into the defined mineral salts medium listed previously) were inoculated and incubated aerobically, in increased $CO_2$ (candle jar), and anaerobically (BBL-GasPak).

TEMPERATURE SCREENING

Pseudomonas MB86 was examined for its optimal growth temperature using 0.25% yeast extract and 4-chlorobiphenyl broth and plates. Cultures were run in duplicate at 20° C., 30° C, 37° C., and 41° C.

FREEZING AND STORAGE OF CULTURES

After purification by repeated streaking on yeast extract plates, one liter of the organism was grown to mid-log phase in 0.25% yeast extract. Cells were concentrated by centrifugation for fifteen minutes at $8000 \times g$ in sterile bottles. After decanting the supernatant solution, 10 ml of fresh, sterile, 0.25% yeast extract were added and the cells resuspended. To each of 13 sterile plastic vials was added 0.75 ml of the cell suspension and 0.25 ml sterile glycerol. The cultures were then frozen at $-70°$ C. for use as stocks.

PH MEASUREMENTS pH measurements were carried out using a Fischer model 825MP digital pH/millivolt meter or Corning model #120 pH meter.

TURBIDITY MEASUREMENTS

Measurements of cell growth in yeast extract broths were performed using a Beckman DU quartz spectrophotometer by determining absorbance of culture fluids at 600 nm. When cultures were grown on 4-chlorobiphenyl as the sole carbon and energy source, turbidity was determined using a Hewlett-Packard diode array spectrophotometer model #8482. Spectra of the compounds present in such cultures were also obtained with this instrument.

GROWTH CURVES

For determination of growth rate in 0.25% yeast extract, several colonies from a stock plate were inoculated into yeast extract broth which was incubated with shaking for approximately 18 hours. One ml of this culture was then added to each of two similar flasks. Samples were taken every thirty minutes and their optical densities at 600 nm determined. During logarithmic growth phase, five samples were taken for determination of viable counts. Samples were diluted into sterile basal medium and the $10^{31\ 6}$ through $10^{-8}$ dilutions were plated in triplicate.

For determination of growth kinetics in 4-chlorobiphenyl broth, several colonies were taken from a stock plate and inoculated into a flask of basal medium containing 4-chlorobiphenyl as the only growth substrate. After three days of incubation, one ml of the initial culture was added to each of two flasks of the same medium. Samples were taken every 24 hours over a period of seven days for determination of absorbance at 600 nm. Due to production of colored compounds, the samples were also spun for five minutes in a Beckman microfuge to remove cells, and the supernatant solutions read again at 600 nm to allow correction for absorption due to organic compounds. Viability counts also were made at various times during the course of the experiment.

TIME COURSE STUDIES FOR PRODUCTION OF METABOLITES

Pseudomonas MB86 was inoculated into each of 14 flasks containing 50 ml of basal medium and 50 mg of 4-chlorobiphenyl. Seven additional flasks contained the substrate, but were not inoculated. Each day, two inoculated flasks and one uninoculated flask were sacrificed. Observations were made on their turbidity ($A_{600}$), purity of the culture, color, and pH. Exhaustive extractions into ethyl ether were performed, as described below, and the extracts analyzed by gas-chromatography (GC).

QUALITATIVE AND QUANTITATIVE EXTRACTIONS

Whole culture extractions were performed using ethyl ether (amounts approximately equaled the total volume of the culture when totally extracted). Samples (total cultures were sacrificed) at neutral pH were extracted for four minutes with vigorous shaking. The water phases were removed, acidified to pH<2 (10% $H_2SO_4$) and re-extracted with ethyl ether. Both extractants were dried for several minutes over anhydrous sodium sulfate and filtered through Whatman #11 filter paper. After evaporation of the ether at 40° C. to near dryness, the samples were taken up into acetone and dispensed into GC vials which were capped and stored in the dark at 4° C. until analyzed (usually not stored more than 3 days). Standard solutions of various expected and/or related compounds (4-chlorobenzoate, acetophenone, 4'-chloroacetophenone, etc.) were prepared by dissolving the compounds in acetone (10 mg/ml).

Following tentative identification of some gas-chromatography peaks considered indicative of 4-chlorobiphenyl metabolites of interest, rigorous quantitive extractions were performed. Here each culture was first acidified to pH<2 (10% $H_2SO_4$), extracted three times into ethyl ether for four minutes each time (vigorous shaking for four minutes), concentrated by evaporation, and taken up into 1 ml of acetone containing an internal standard (60 ppm, 2'-chloroacetophenone). Such a technique was utilized for time course as well as one time studies. Solutions were stored in the dark at 4° C. until analyzed.

In an attempt to isolate multi-milligram amounts of 4-chlorobiphenyl metabolites, 1L cultures were extracted exhaustively with ether. This was done to insure that as much of the products as possible were extracted. After purification by preparative TLC described herein, unknown metabolites were analyzed by gas-chromatography/mass-spectroscopy (GC/MS). This method was later altered to separate base/neutrals from acidic compounds. The 1L culture was filtered to remove excess 4-chlorobiphenyl. Approximately 50 g of sodium bicarbonate were added to the culture. This was followed by exhaustive extraction into ethyl ether. The water phase was then acidified to pH 2 with 10% $H_2SO_4$, exhaustively extracted into ether, and back extracted with 5% $NaHCO_3$ to remove any base/neutrals that may have been present. After removal of ether by evaporation, the residues were taken up into 20 ml of ethyl ether and examined using analytical thin-layer chromatography (TLC) and/or preparative TLC. Organic compounds were located on TLC plates by observation under ultraviolet light (254 nm). Spots or bands were scraped from the plates and compounds eluted from the silica gel with a small amount (10-20 ml) of ether or acetone.

THIN LAYER CHROMATOGRAPHY (TLC).

Initially, TLC silica gel sheets containing a fluorescent indicator were utilized. They were developed with a solvent mixture containing: toluene: ethyl acetate: formic acid (85:15:1 by volume). Analytical chromatograms were sprayed with Gibbs' reagent (.05% N-2,6-trichloro-p-benzoquinone imine in ethanol for detection of phenols and with 10.4% 2,4-dinitrophenylhydrazine in 2N HCl for detection of ketones.

TLC analytical and larger preparative plates were employed for the isolation of 4-chlorobiphenyl metabolites. The solvent used here was toluene: ethylacetate: formic acid (90:9:1, volume/volume). Bands of organic compounds were located by observing their quenching of plate fluorescence under 254 nm light.

GAS-CHROMATOGRAPHY

Analyses of metabolites in ether extracts of culture media also were performed using a Hewlett-Packard gas-chromatograph model #5790A. A 5% phenyl methyl silica capillary column was employed with a flame ionization detector (FID) for peak detection. Hydrogen was the carrier gas. A temperature program was used, with a range of 80° C. to 300° C., with an increase of 8° C./minute. Injector temperature was 225°

C. With rare exceptions, these conditions yielded peaks that were well-defined and well-separated.

SAMPLE PREPARATION FOR MASS-SPECTROSCOPY (MS)

Cultures were exhaustively extracted into ethyl ether and the ether extract then concentrated by evaporation at 40° C. The organic residues were taken up with 3 ml of ethyl ether. Using a Pasteur pipette, drawn out to a capillary, dissolved residues were loaded onto TLC preparative plates. Standards of 4'-chloroacetophenone and 4-chlorobiphenyl were spotted, one on each side of the plate. The plates were then developed in the appropriate solvent (see above). After drying the plates, separated compounds, seen as bands, were scraped from the plates into individual beakers where the silica gel was first suspended in acetone and then filtered. An aliquot of the filtrate was then spotted onto an analytical plate to examine the purity of each extracted compound. If judged pure (one spot), the sample was evaporated to dryness and taken up into 2 ml of fresh acetone and sent out for mass-spectral analysis. If the sample was judged to be impure (multiple spots), preparative TLC was repeated.

GLC/MASS-SPECTROSCOPY

Following establishment of proper separation conditions using the Hewlett-Packard GC, some samples were analyzed on a Krator GLC/MS 25 mass-spectrometer/gas-chromatograph. Ionization energy was set at 70eV. Samples which were thought to contain carboxylic acid moieties were derivatized with trimethylsilane (TMS) prior to GLC/MS analysis.

SAMPLE PREPARATION FOR NUCLEAR MAGNETIC RESONANCE SPECTROSCOPY (NMR) OF 4'-CHLOROACETOPHENONE

Cultures were extracted as above into ethyl ether. After evaporation of the ether, samples were taken up into 3 ml of ethyl ether, streaked onto a TLC preparative plate, and chromatographed. Several bands were observed, the band that corresponded with the 4'-chloroacetophenone standard was removed, suspended in ethyl ether, and filtered through a fritted glass filter. The filtrate was then evaporated to dryness, redissolved in 2 ml of deuterated chloroform ($CDCl_3$), and evaporated to dryness again. One ml of $CDCl_3$ was added, the solution placed into a 10 mm NMR tube, and sent out for analysis by NMR spectroscopy. Standard compounds were prepared at 100 mM concentration in ether (1 ml), evaporated to dryness, and taken up in 1 ml of $CDCl_3$. Samples were examined at 300 mHz with TMS as a reference using the spectrometer facilities in the Department of Biochemistry, St. Paul (Model, Nicollet NT-300 WB).

ENZKYME ASSAYS

One liter of cells grown to approximately mid-logarithmic phase on 4-chlorobiphenyl and one liter grown to late mid-logarithmic phase on 0.25% yeast extract were harvested by centrifugation, washed with cold buffer (phosphate, pH 7.0, 50 mM), resuspended in a small volume of cold buffer, and lysed by passing through a pre-chilled French Press at 20,000 psi. The lysed cell suspension was centrifuged at $20,000 \times g$ at 4° C. for fifteen minutes using a Sorvall centrifuge. The enzyme extracts were kept on ice and assayed immediately for their abilities to catalyze oxygen consumption when presented with 4-phenylpryocathechol (Kodak Chemicals). Assays were run in a thermostatic chamber equipped with a Clarke electrode (Yellow Springs Instruments). Assay mixtures contained 1 ml of buffer (50 mM $PO_4$, pH 7.0), 100ul of cell-free extract (1mg protein) and 5 umole of 4-phenylpyrocatechol. The reaction was initiated by addition of substrate. Oxygen uptake was corrected for uptake observed with cell extract alone.

PLASMID MINIPREPS

To examine bacterial cells for the presence of plasmids, the alkaline lysis method of Ish-Horowitz (Maniatis, et al., *Molecular Cloning*, p. 368–369 (Spring Harbor Laboratory Publications (1982)) was employed. Agarose gels were 0.7% and each well contained 10 ul of the prepared sample. Lambda DNA restricted with HindIII and with BstEII served as molecular markers. *Escherichia coli* mini-preps containing pBR322 served as a control to insure the gel electrophoresed properly. Eletrophoresis took place at 25V overnight. The gel was then stained with 0.0001% ethidium bromide for 45 to 60 minutes, rinsed with distilled water, and photographed with a Polaroid camera using a UV filter.

MUTAGENESIS AND PLASMID CURING

Fifty microliters of a mid-logarithmic phase culture of the bacterium were added to each of ten test tubes containing 0.25% yeast extract and one of the following agents: acridine orange, novabiocin, mitomycin C, or ethidium bromide. Tubes containing the latter two compounds were wrapped tightly in foil and incubated in the dark to prevent photoinactivation of the curing-/mutagenic agent. Controls, containing only yeast extract, were also used. Cultures were checked each day for growth and transferred to a new series of test tubes of the same medium and curing agent, except that curing agents were added at slightly increased concentrations at each transfer. After several passages, dilution platings were done in triplicate on 0.25% yeast extract agar. Once colonies appeared on plates, replica plating was done to determine if any colonies had become unable to utilize 4-chlorobiphenyl as a growth substrate. Suspected cured or mutant cell lines were patched from master plates to a new yeast extract plate and to a plate containing 4-chlorobiphenyl as the sole carbon and energy source. After incubation, cell lines that failed to grow on the 4-chlorobiphenyl plates were streaked onto another yeast extract plate and subsequently inoculated into 4-chlorobiphenyl broths. Failure to grow in such a broth was considered proof of inability to utilize the substrate.

ELECTRON MICROSCOPY

Bacterial cells were placed on a paladiumcoated electron microscope grid and negatively stained with phosphotungstic acid by standard procedures. Stained cells were viewed and photographed using a Phillips 201 transmission electron microscope. These facilities were located at the University of Minnesota, Department of Biology, St. Paul, Minnesota.

CHEMICALS

Chemicals were purchased as follows: acetophenone, 2'-chloroacetophenone, 3'-chloroacetophenone, 4'-chloroacetophenone, 3-chlorobenzoic acid, 4-chlorobenzoic acid, and 3,5-dichlorobenzoic acid from the Aldrich Chemical Co.; 4-chlorobiphenyl from Pfaltz and Bauer, recrystallized from absolute ethanol;

2-chlorobiphenyl from Pfaltz and Bauer; 3-chlorobiphenyl from Alfa Products; biphenyl from Mallinckrodt; 4-hydroxybenzoate from Eastman; 4-phenylpyrocatechol from Kodak.

ISOLATION OF PSEUDOMONAS MB86.

Pseudomonas MB86 was isolated from soil contaminated with creosote and pentachlorophenol, obtained in an industrial area of southern New Brighton, Minn.

Approximately one gram of the contaminated soil was added to each of three, 125 ml Erlenmeyer flasks containing 50 ml of basal medium containing 0.05% (weight/volume) 4-chlorobenzoate. These flasks were incubated on a shaker at 30° C. for one week. Microscopic analysis at this time revealed a variety of microorganisms. One hundred microliters of each enrichment were spread onto each of three agar plates containing 0.05% 4-chlorobenzoate. Three agar plates containing basal medium, but no growth substrates were inoculated with 100 ul of the 4-chlorobenzoate enrichment. Approximately 10.0 mg of 4-chlorobiphenyl were placed in the lids of each of these plates Colonies that appeared on these plates were then restreaked several times on 1% yeast extract agar plates for purification. Pure cultures obtained from yeast extract plates after 2-3 days were then streaked onto plates with 4-chlorobiphenyl as the sole carbon source and incubated for 4-10 days.

After 4 days, one bacterium, later identified as Pseudomonas MB86, produced a characteristic yellow/brown color on 4-chlorobiphenyl medium. The plates also had a sweet smell. Colonies were very small and opaque on the minimal medium. On yeast extract the bacterium produced light yellow colonies. Once purified, the bacterium was grown in quantity, concentrated, and frozen for stock cultures using the materials and methods described herein.

IDENTIFICATION AND CHARACTERIZATION OF THE 4-CHLOROBIPHENYL DEGRADING BACTERIUM

The purified 4-chlorobiphenyl medium isolate described above was characterized for morphologic and physiologic traits as described below.
Morphology: rod shaped, motile with single polar flagellum at the cell terminus
Gram Stain: negative
Physiology: positive with respect to catalase and oxidase; non-fermentive as indicated by triple sugar iron media The bacterium was inoculated into an OxiFerm tube (Roche Labs), as was a known Pseudomonas species (*P. aeruginosa*). After 24 and 48 hours various tests in the tubes were scored as indicated in Table 1 below:

TABLE 2

| Medium | Observations |
|---|---|
| Biphenyl | (p) scant growth; (l) scant growth |
| 2-chlorobiphenyl | (p) no growth; (l) no growth |
| 3-chlorobiphenyl | (p) growth; (l) ND |
| 4-chlorobiphenyl | (p) growth, yellow/brown pigment; (l) same as (p) |
| 3-chlorobenzoate | (p) no growth; (l) no growth |
| 3,5-dichlorobenzoate | (p) no growth; (l) no growth |
| p-hydroxybenzoate | (p) ND; (l) no growth |
| benzoate | (p) ND; (l) no growth |
| 4'-chloroacetophenone | (p) no growth; (l) no growth |

Results from media inoculated with *Pseudomonas* MB86.
(p) = plate;
(l) = broth.

Based on the above morphologic and physiologic traits the purified 4-chlorobiphenyl degrading bacteria isolated from the creosote and pentachlorophenol contaminated soil described herein was determined to be a strain of Peudomonas appropriately classified as Psudomonas MB86. The purified culture of Psudomonas MB86 has been deposited with the American Type Culture Collection, Rockville, Md., and has been assigned ATTC No. 53728.

GROWTH CURVE OF PSUDOMONAS MB86 IN 0.25% YEAST EXTRACT BROTH.

In order to gain information pertaining to the organism's generation time on a rich carbon source, cell densities of 2 freshly inoculated 0.25% yeast extract cultures were measured over an eight hour period. As can be seen in FIG. 1 (data points represent average values of duplicate flasks), growth progressed in the expected three phase pattern of lag, log, and stationary phases. Death phase was not observed in this time period. Cell doubling time was determined from the growth curve during logarithmic phase and shown to be approximately two hours. Viable counts revealed that during logarithmic phase, cell densities of approximately $10^9$ cells per ml were obtained.

GROWTH CURVE OF PSUDOMONAS MB86 ON 4-CHLOROBIPHENYL

Figure 2:
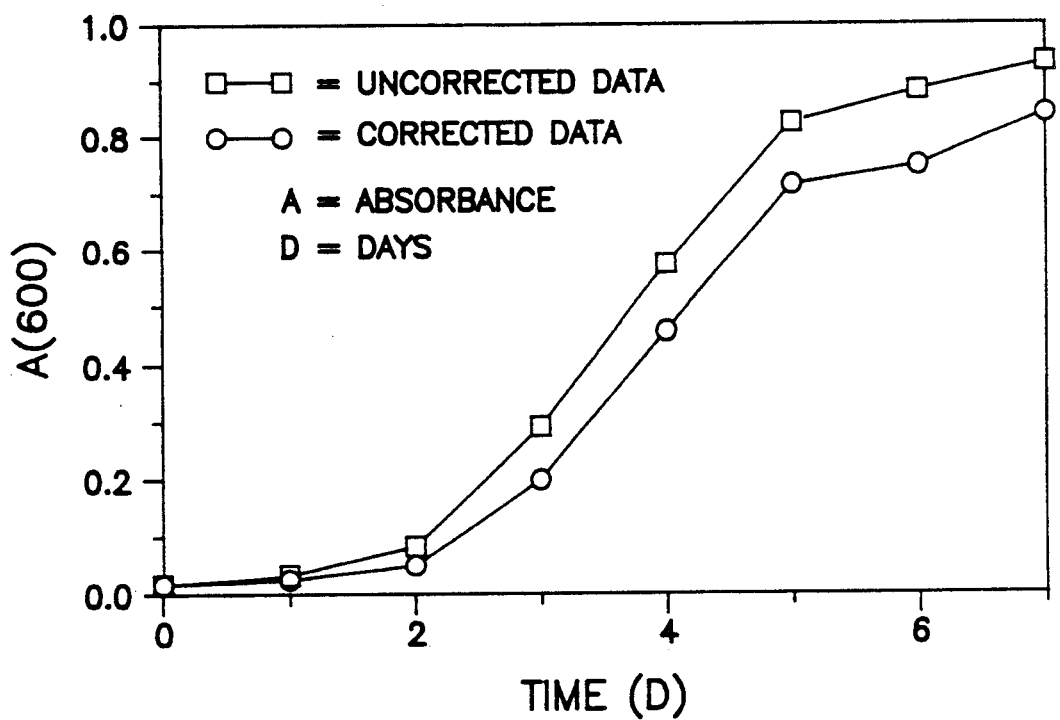
FIG. 2 shows a growth curve of Pseudomonas MB86 in 4-chlorobiphenyl broth.

To determine the rate at which Pseudomonas MB86 grew on 4-chlorobiphenyl as the sole carbon and energy source, flasks were inoculated in duplicate with 4-chlorobiphenyl-induced cells (1 ml per 50 ml of medium). Samples were taken every 24 hours for turbidity measurements. As seen in FIG. 2 (data points represent average values of duplicate flasks), the doubling time increased substantially from that observed for growth in 0.25% yeast extract. No lag phase was apparent, but both the logarithmic and stationary phases were observed. Cell doubling time was approximately 14 hours

TABLE 1

| Organism | Oxidase | Anaerobic (Dextrose) | Arginine | $N_2$ Gas | $H_2$ Gas | Indole | Xylose | Aerobic (Dextrose) | Urea | Citrate |
|---|---|---|---|---|---|---|---|---|---|---|
| MB86 | + | − | − | − | − | − | − | − | − | − |
| Control (*P. aeruginosa*) | + | − | + | − | − | − | + | − | + | − |

Results from 24 hour incubation of OxiFerm tubes.
(+) = positive reaction growth
(−) = no reaction, no growth To further characterize the organism's ability to grow on various compounds other media prepared as described herein were utilized and growth observations are reported in Table 2 below:

and viable counts revealed approximately $10^8$ cells per ml at midlogarithmic phase.

During growth on 4-chlorobiphenyl, colored compounds were produced. To determine if these compounds affected readings at 600 nm, samples were centrifuged for five minutes in a Beckman microfuge and the absorbance of the supernatant solution at 600 nm determined. Absorbance values were recorded and substracted from turbidity readings. (FIG. 2). Also, it appeared that the appearance of color in culture fluid coincided with cell growth.

IDENTIFICATION OF 4'-CHLOROACETOPHENONE

Figure 3:
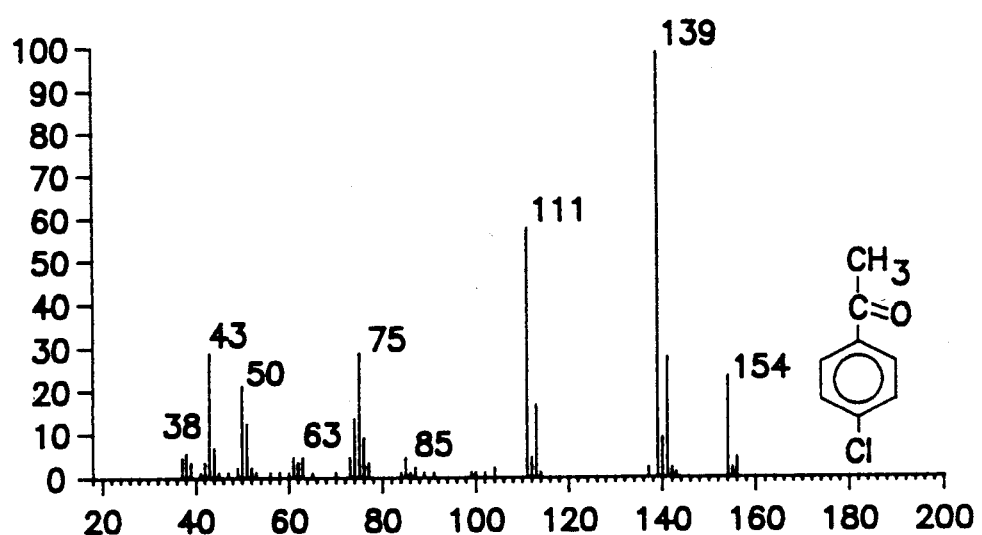
FIGS. 3-4 show a gas-chromatograph/mass spectra of a 4'-chloroacetophenone standard and metabolite extracted from Pseudomonas MB86 culture fluid, respectively.
Figure 4:
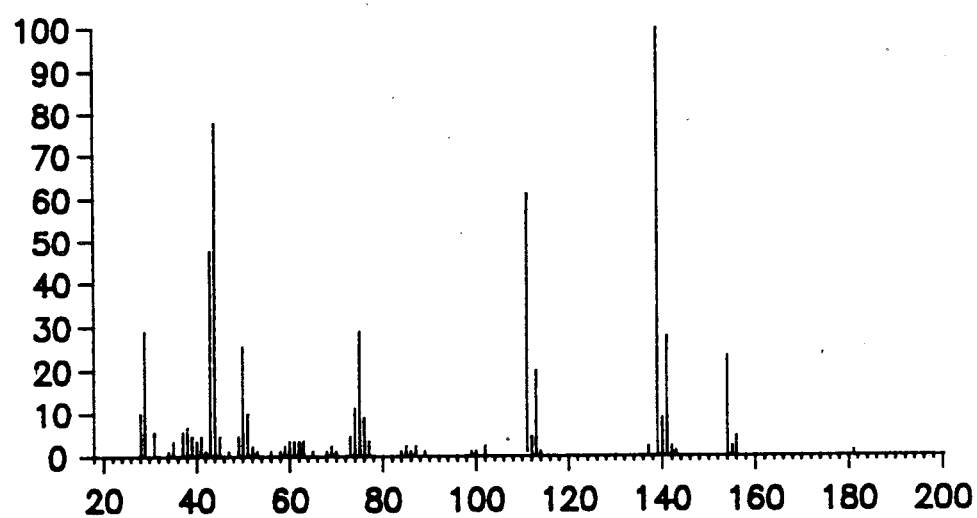
Figure 5:
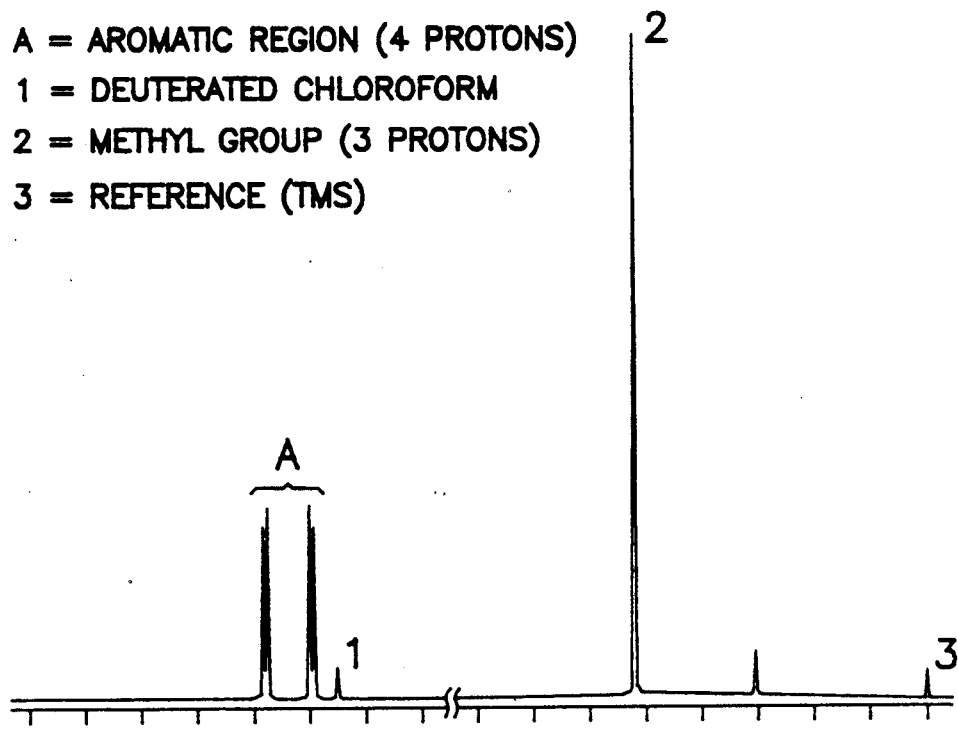
FIGS. 5-6 show Nuclear Magnetic Resonance (NMR) spectra of 4'-chloroacetophenone standard and metabolite extracted from Pseudomonas MB86 culture fluid, respectively.
Figure 6:
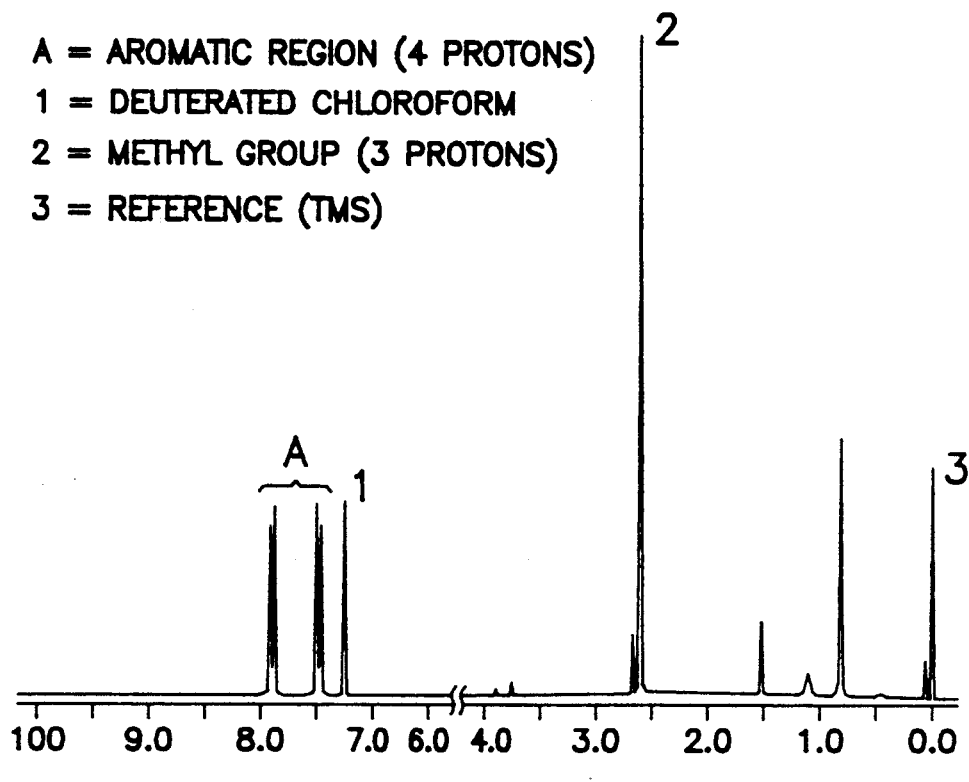
Figure 7:
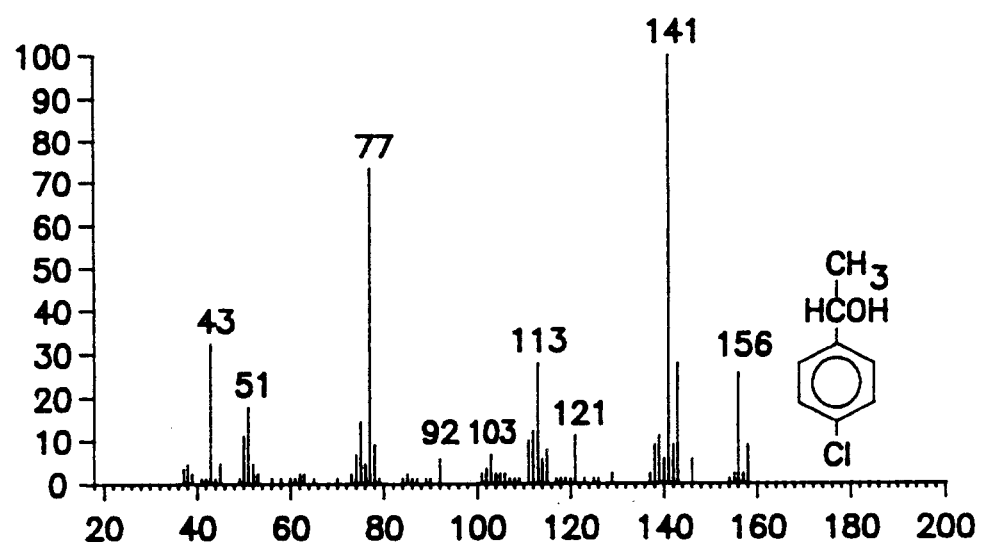
Figure 8:
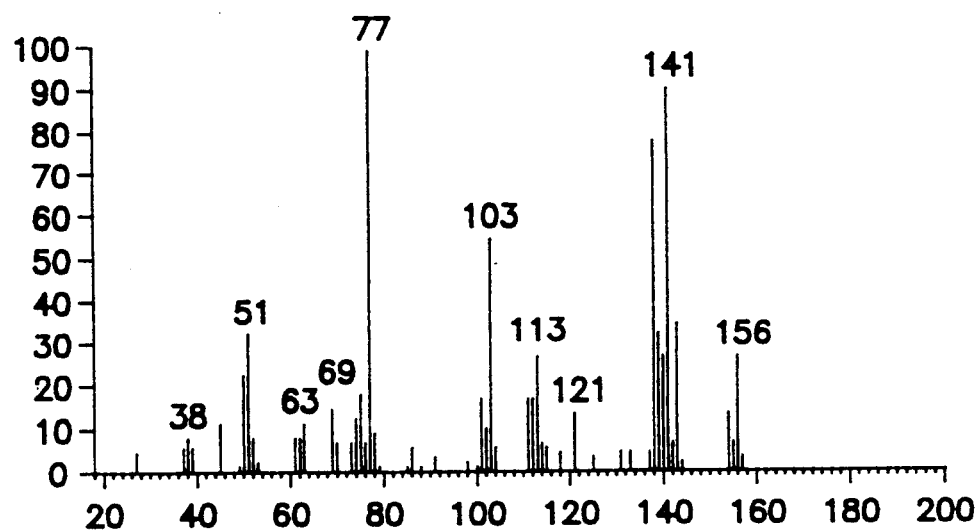
Figure 9:
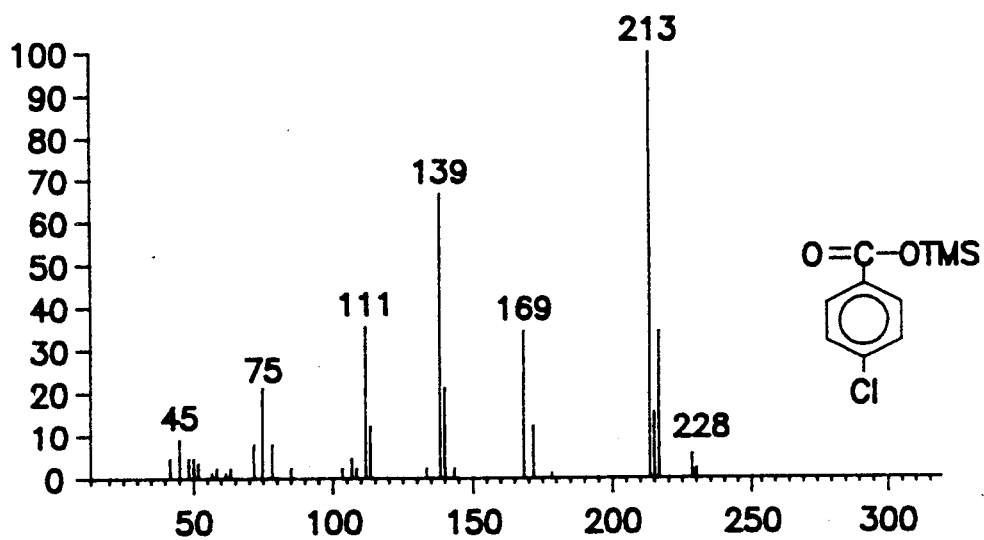
FIGS. 9-10 show gas-chromatograph/mass spectra of 4-chlorobenzoate standard and metabolite extracted from Pseudomonas MB86 culture fluid, respectively.
Figure 10:
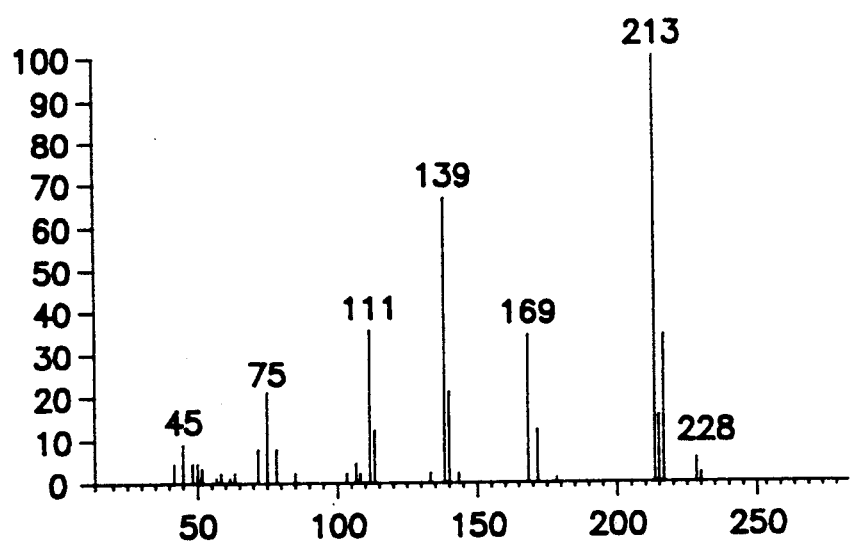

During growth of Pseudomonas MB86 in the presence of 4-chlorobiphenyl, a very sweet smell was noted. The odor faded with time. Gas-chromatography of ether extracts of culture fluids revealed several peaks indicative of 4-chlorobiphenyl metabolites. A major peak had the same retention time as known 4'-chloroacetophenone. As shown in FIG. 4, gas-chromatography/mass-spectroscopy of the unknown revealed an essentially identical fragmentation pattern as that seen for known 4'-chloroacetophenone run as a standard (FIG. 3). The metabolite was extracted from larger culture volumes (1L), purified by preparative TLC and analyzed by NMR spectroscopy. As seen in FIGS. 5 and 6, the purified metabolite had an NMR spectrum identical to known 4'-chloroacetophenone. These experiments confirmed that Pseudomo as MB86 produced 4'-chloroacetophenone.

PRELIMINARY IDENTIFICATION OF ADDITIONAL METABOLITES

Preparative TLC revealed, in addition to bands for 4-chlorobiphenyl and 4'-chloroacetophenone, an additional well-defined band. This metabolite was isolated and prepared for GLC/MS analysis. GLC indicated the presence of several compounds. Two of these were initially identified as 2-hydroxy,2-[4'-chlorophenyl]ethane and 4-chlorobenzoic acid. As shown in FIGS. 7-10, upon comparison to known standards, identification was confirmed. In the case of the 4-chlorobenzoic acid, a TMS derivitized sample was compared with a TMS derivitized standard. Another chlorinated compound was found and was consistent with the structure.

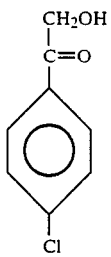

Figure 11:
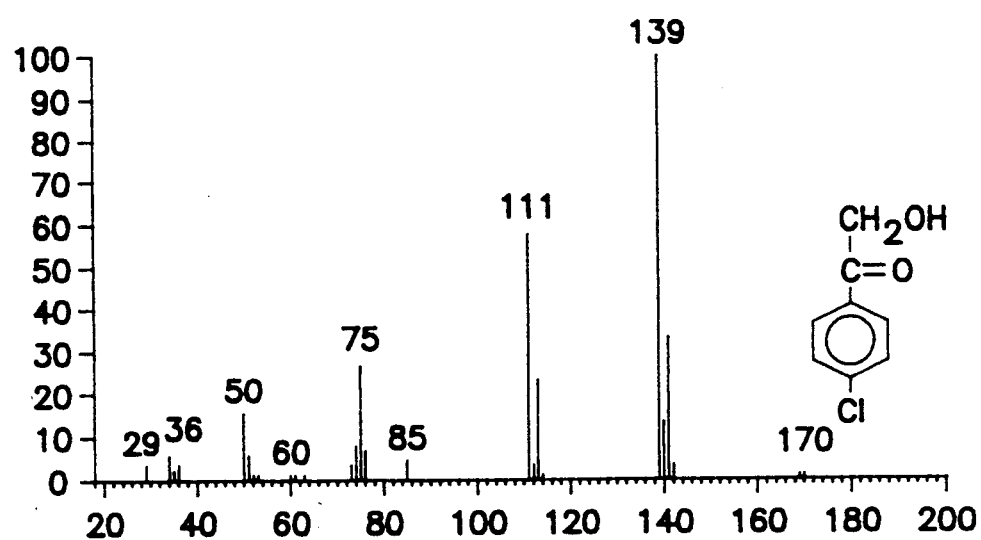
FIG. 11 shows mass spectrum of 2-oxo, 2-[4'chlorophenyl] ethanol-tentative identification.

Mass spectral data (FIG. 11) indicated a molecular ion (M+) of 170, and an M+(—CH$_2$OH) of 139, with a subsequent fragmentation pattern identical to the M+(—CH$_3$) of 4'-chloroacetophenone. This compound was tentatively identifed as 2-oxo, 2-[4'-chlorophenyl] ethanol.

TIME COURSE STUDIES

Figure 12:
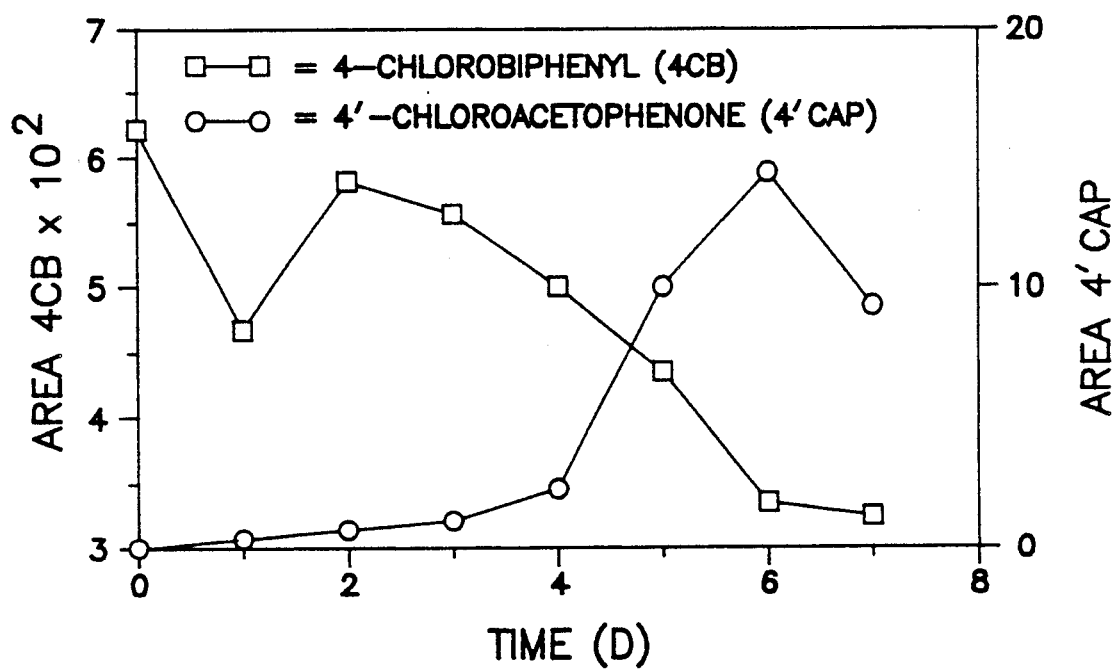
FIG. 12 shows results of GC analysis of extracted Pseudomonas MB86 culture fluids over a seven day period.

Data from a seven day growth experiment of Pseudomonas MB86 on 4-chlorobiphenyl confirmed the importance of 4'-chloroacetophenone as a 4-chlorobiphenyl metabolite. GC analyses indicated a decline in 4-chlorobiphenyl concentration over time, with a concurrent increase in 4'-chloroacetophenone concentration. As shown in FIG. 12, (data points represent average values obtained after normalization to the internal standard 2-chloroacetophenone) in several cases at day 6 this production of 4'-chloroacetophenone peaked and began to decline to day 7.

An interesting aspect of these time course experiments was the predictable color change that occurred. Twenty-four to thirty-six hours after inoculation, the cultures exhibited a lilac color. Spectrophotometric analysis revealed a peak in the range of 532 nm. Upon acidification at pH<2 with 10% H$_2$SO$_4$, this color disappeared. Upon addition of base (6N NaOH) to pH>10, no change was noted. The compound was quickly reduced (decolorized) with a small amount of sodium borohydride and easily reoxidized (color recovered) with 3% H$_2$O$_2$. These data suggest the presence of a quinone.

Figure 13:
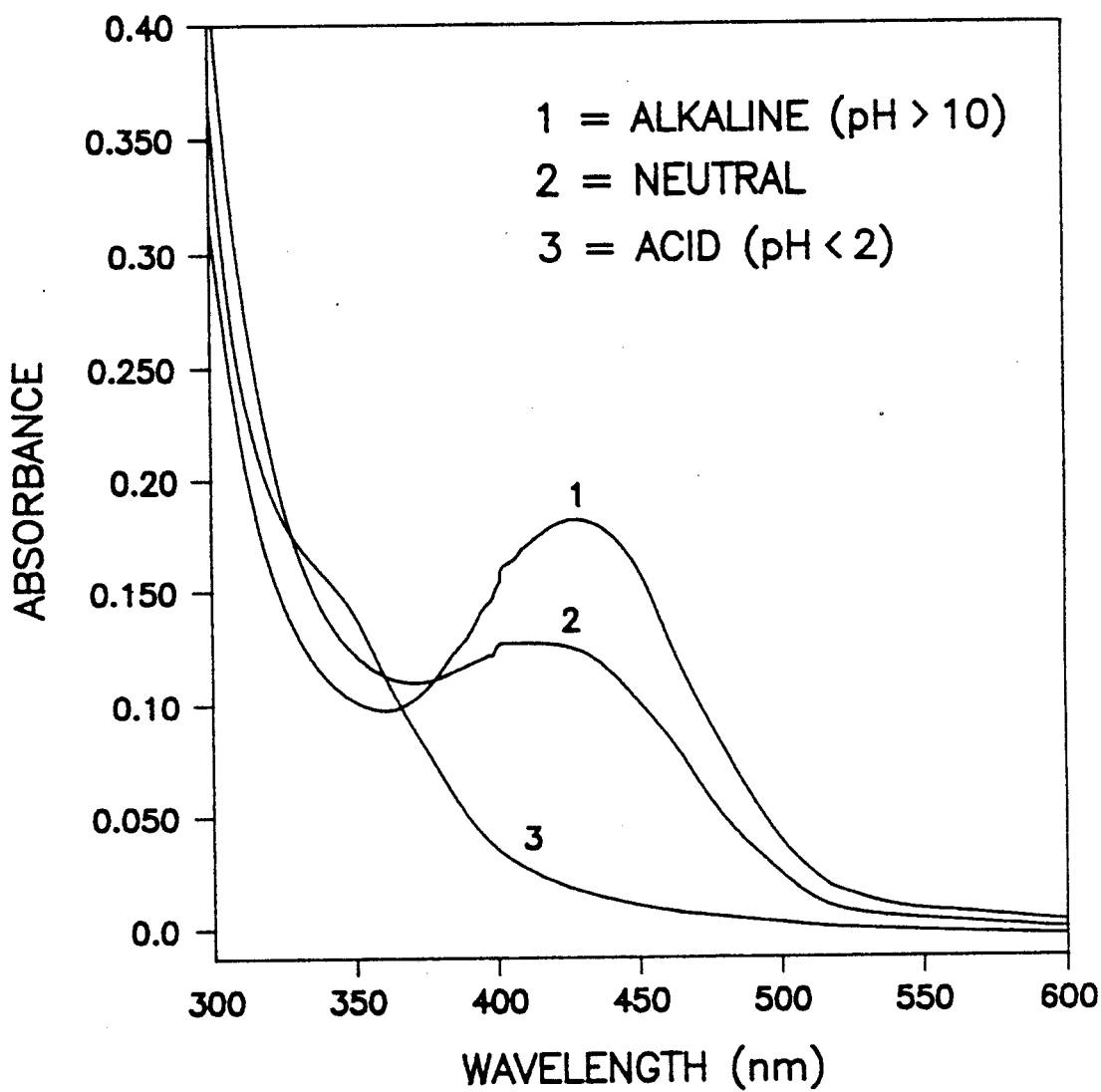
FIG. 13 shows spectra of ring fission product in various pHs.

Within 48 hours, the cultures exhibited a golden color. This gradually darkened over time until at seven days the cultures took on an olive color. Heavy inoculation of the organism from a stock plate produced a brilliant yellow color within 24 hours. Upon acidification to pH<2 10% H$_2$SO$_4$, the color bleached. As seen in FIG. 13, in alkaline conditions of pH>10, the color intensified. This indicates the presence of a ring fission product such as muconic semialdehyde (Gibson, *Science*, 161:1093–1097 (1968); Furukawa and Matsumura, *J. Agric. Food Chemistry*, 24:251–256(1976)). As seen further in FIG. 13, spectral analysis at neutral, acidic, and basic pH's revealed a shift in wavelength.

PLASMID PREPS.

As seen in FIG. 14, electrophoresis of alkaline "miniprep" lysates of Pseudomonas MB86 showed five or six DNA bands. This pattern was reproducible. These bands may represent individual plasmids, or different forms of a plasmid.

MUTAGENESIS AND PLASMID CURING

The organism failed to show viability in as little as 1 ug/ml of mitomycin C. Growth in acridine orange was noted, but upon subculturing viability was lost. The organism was successfully subcultured through increasing amounts of ethidium bromide (EtBr) (up to 50 ppm) and Novobiocin (up to 21 ppm). Replica plating of cells surviving subculturing through five transfers in media containing these curing agents/mutagens revealed the presence of two potential mutants or cured strains from the ETBr series and seven from the Novobiocin series. Approximately 110 colonies were screened from both series. Further testing of the potential mutants revealed only five that could not grow on 4-chlorobiphenyl. All five were from the Novobiocin series.

What is claimed is:

1. A biologically pure culture of Pseudomonas MB86 having the identifying characteristics of ATCC 53728, and mutants which are capable of utilizing 4-chlorobiphenyl as a sole carbon and energy source and degrading 4-chlorobiphenyl to chloroacetophenone and other metabolites.

* * * * *

UNITED STATES PATENT AND TRADEMARK OFFICE
CERTIFICATE OF CORRECTION

PATENT NO. : 4,999,300

DATED : March 12, 1991

INVENTOR(S) : Marlene R. Barton

It is certified that error appears in the above-identified patent and that said Letters Patent is hereby corrected as shown below:

At column 1, before the section "Technical Field", insert the following section:

--Government Support

This invention was made with government support under grants NOAA-86AA-D-SG112 and NA85AA-D-SG136 by the Minnesota Sea Grant Program, National Oceanic and Atmospheric Administration Office of Sea Grant, U.S. Department of Commerce. The government has certain rights in the invention.--

At column 1, line 20, for "congenersẑ" read --congeners--

At column 2, line 42, for "chlorohiphenyl" read --chlorobiphenyl--

At column 3, line 20, for "714 8" read --7-8--

At column 3, line 39, for "desiqnated" read --designated--

At column 3, line 40, for "MB8 6" read --MB86--

At column 5, line 23, for "$10^{31\ 6}$" read --$10^{-6}$--

At column 7, line 57, for "ENZKYME" read --ENZYME--

At column 10, line 20, for "Psudomonas" read --Pseudomonas--

At column 10, lines 20-21, for "Psudomo-nas" read --Pseudomonas--

At column 10, line 23, for "ATTC" read --ATCC--

At column 10, line 25, for "PSUDOMONAS" read --PSEUDOMONAS--

UNITED STATES PATENT AND TRADEMARK OFFICE
CERTIFICATE OF CORRECTION

PATENT NO. : 4,999,300
DATED : March 12, 1991
INVENTOR(S) : Marlene R. Barton It is certified that error appears in the above-identified patent and that said Letters Patent is hereby corrected as shown below:

At column 10, line 41, for "PSUDOMONAS" read --PSEUDOMONAS--

At column 11, line 5, for "substracted" read --subtracted--

At column 11, line 26, for "Pseudomo as" read --Pseudomonas--

At column 11, line 57, for the first "(M+)" read --($M^+$)--

At column 11, line 57, for the second " M+ " read --($M^+$)--

At column 11, line 59, for " M+ " read --($M^+$)--

Signed and Sealed this

Eleventh Day of January, 1994

*Attest:*

BRUCE LEHMAN

*Attesting Officer*     *Commissioner of Patents and Trademarks*